United States Patent [19]
Chul

[11] Patent Number: 5,256,151
[45] Date of Patent: Oct. 26, 1993

[54] SAFETY SYRINGE WITH RETRACTIBLE NEEDLE HOLDER

[75] Inventor: Bang Y. Chul, Seoul, Rep. of Korea

[73] Assignee: Mediverse, Inc., St. Paul, Minn.

[21] Appl. No.: 973,556

[22] Filed: Nov. 9, 1992

Related U.S. Application Data

[63] Continuation of Ser. No. 885,903, May 18, 1992, abandoned, which is a continuation of Ser. No. 538,248, Aug. 30, 1990, abandoned.

[30] Foreign Application Priority Data

Jun. 15, 1989 [KR] Rep. of Korea .................. 8290

[51] Int. Cl.⁵ .......................... A61M 5/32; A61M 5/00
[52] U.S. Cl. ................................... 604/195; 604/241
[58] Field of Search ............... 604/110, 192, 195, 196, 604/198, 240, 241, 263

[56] References Cited

U.S. PATENT DOCUMENTS

| | | | |
|---|---|---|---|
| 3,890,971 | 6/1975 | Leeson et al. | 128/218 R |
| 4,026,287 | 5/1977 | Haller | 128/215 |
| 4,391,272 | 7/1983 | Staempfli | 604/110 |
| 4,507,117 | 3/1985 | Vining et al. | 604/196 |
| 4,650,468 | 3/1987 | Jennings, Jr. | 604/110 |
| 4,675,005 | 6/1987 | DeLuccia | 604/110 |
| 4,710,170 | 12/1987 | Haber et al. | 604/110 |
| 4,743,233 | 5/1988 | Schneider | 604/192 |
| 4,747,830 | 5/1988 | Gloyer et al. | 604/110 |
| 4,752,290 | 6/1988 | Schramm | 604/198 |
| 4,781,684 | 11/1988 | Trenner | 604/110 |
| 4,861,338 | 8/1989 | Mathiesen et al. | 604/110 |
| 4,888,002 | 12/1989 | Braginetz et al. | 604/195 |
| 4,932,939 | 6/1990 | Magre et al. | 604/110 |
| 4,950,241 | 8/1990 | Rawford | 604/110 |
| 4,950,243 | 8/1990 | Estruch | 604/110 |
| 4,955,869 | 9/1990 | Bin | 604/195 |
| 4,978,340 | 12/1990 | Terrill et al. | 604/195 |
| 4,986,813 | 1/1991 | Blake, III et al. | 604/110 |
| 4,995,874 | 2/1991 | Strickland | 604/195 |
| 5,019,043 | 5/1991 | Segui Pastor et al. | 604/110 |
| 5,030,208 | 7/1991 | Novacek et al. | 604/195 |
| 5,141,500 | 8/1992 | Hake | 604/198 |

Primary Examiner—John D. Yasko
Assistant Examiner—Adam J. Cermak
Attorney, Agent, or Firm—Roger W. Jensen

[57] ABSTRACT

A safety syringe having a hollow barrel member with first and second open ends and female threads on the inside surface of the first end. A special cylindrically shaped needle holder body is positioned inside the first end of the barrel. The holder body has male threads on the curved outer surface thereof adapted to coact with the female threads, and a needle receiving member on one end for receiving and holding a standard hollow needle. The special holder also has a recess in the other end, a first torque transmitting member located in the recess, and a central bore. An elongated piston rod has at one end a piston having, at the distal end, an integral central axially extending protrusion adapted to fit within the recess of said needle holder body, the protrusion having a second torque transmitting member adapted to coact with said first torque transmitting member, and a locking member adapted to coact with said body.

2 Claims, 4 Drawing Sheets

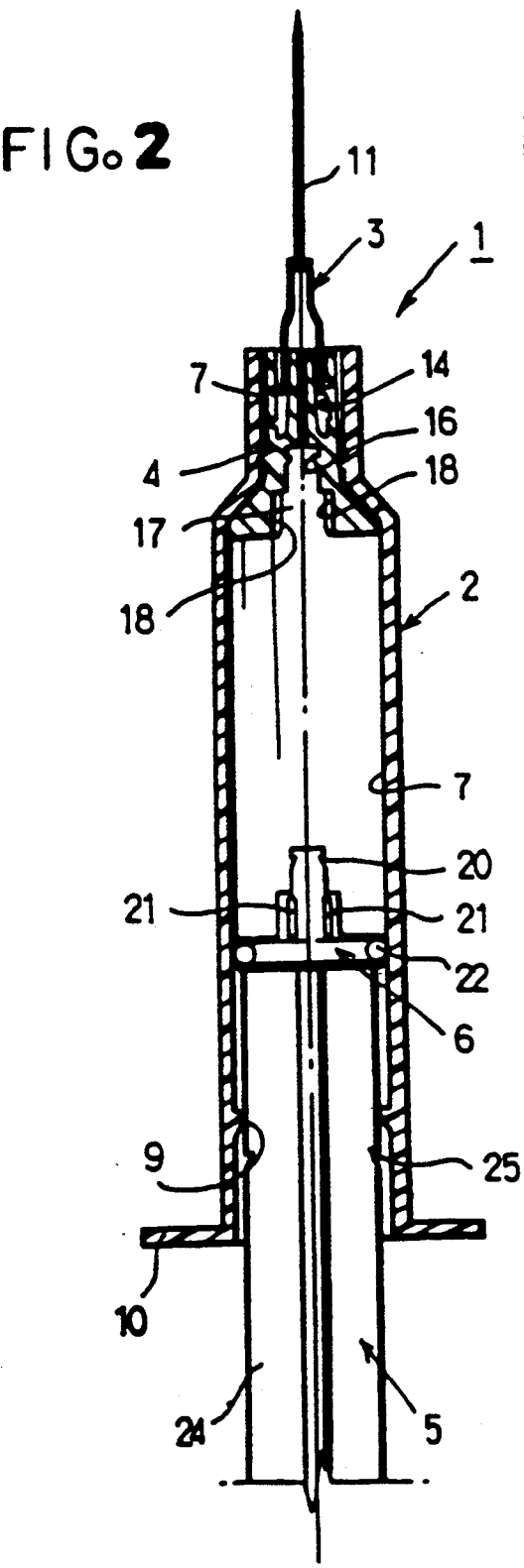
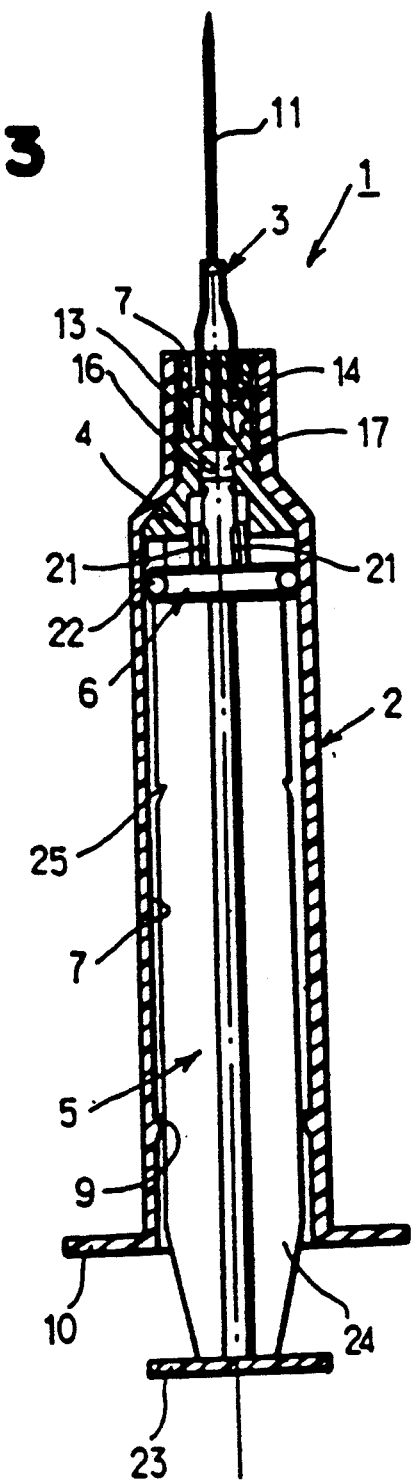

FIG. 4
FIG. 5
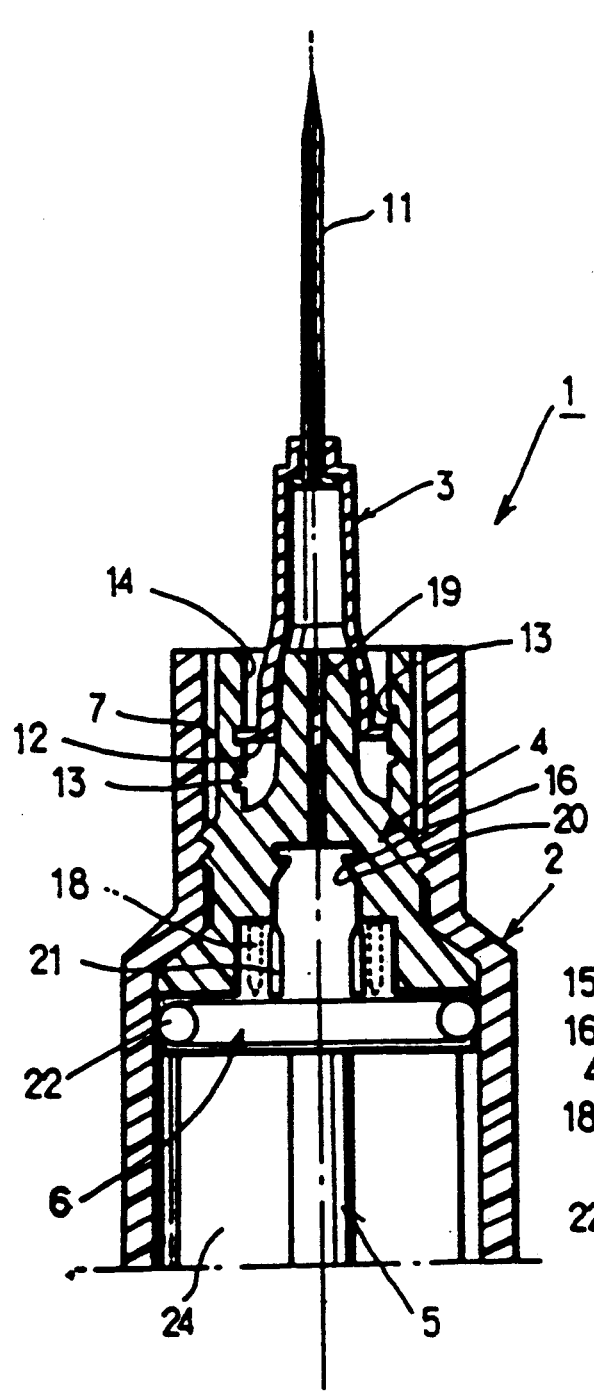
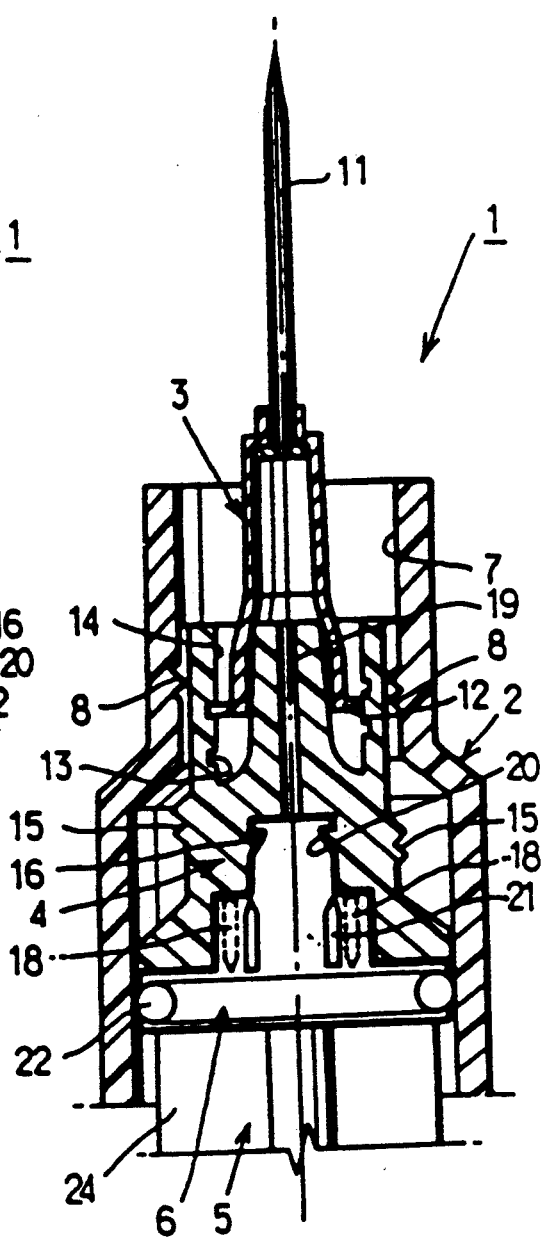

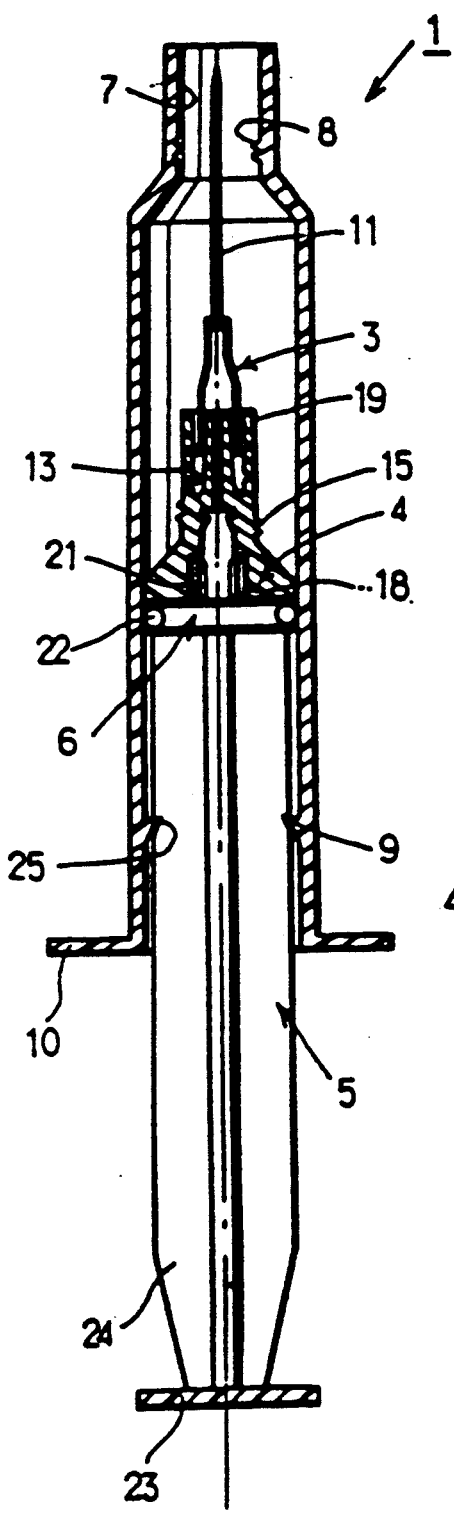
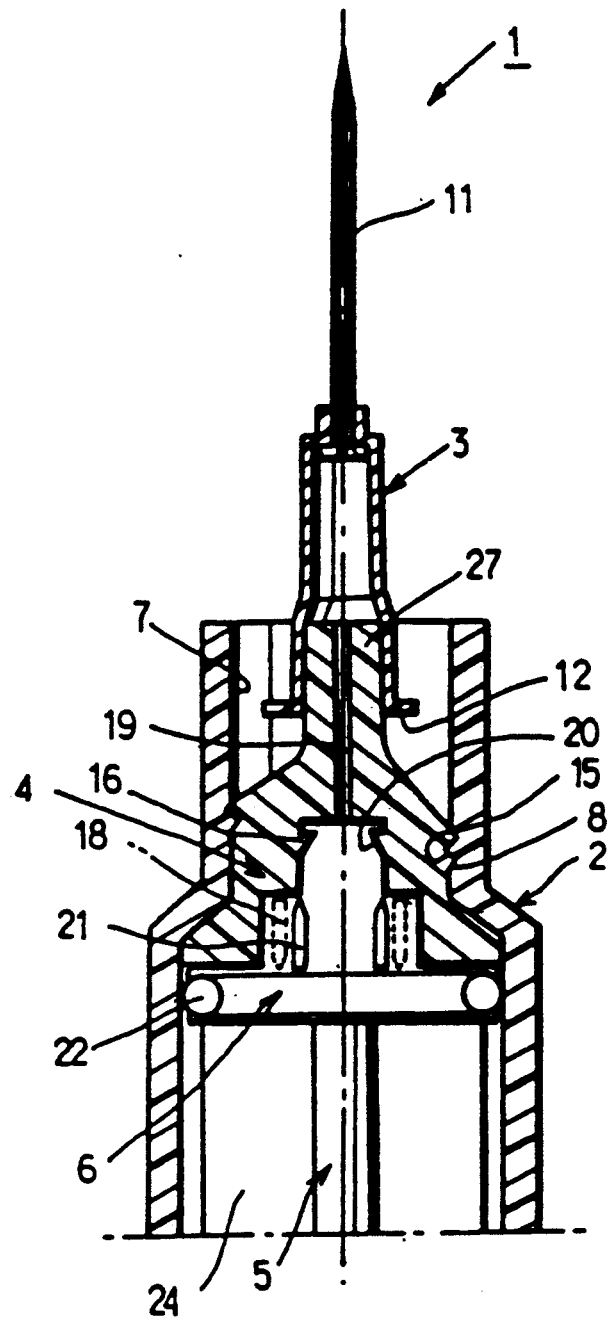

5,256,151

SAFETY SYRINGE WITH RETRACTIBLE NEEDLE HOLDER

This application is a continuation of application Ser. No. 07/885,903, filed May 18, 1992, now abandoned, which is a continuation of application Ser. No. 07/538,248, filed Aug. 30, 1990, now abandoned.

BACKGROUND OF THE INVENTION

This invention relates to hypodermic syringes of the disposable type and to a syringe which will shield the syringe needle from sticking or pricking persons handling the syringe after the syringe has been used.

In the medical field, a health hazard known as "needle stick" exists because a "standard" hypodermic syringe does not have the safety features as would prevent a used syringe from accidently sticking (puncturing) the flesh of medical, clean up, and/or other personnel before the syringe is finally discarded.

The needle stick hazard, of course, incurs the possibility of transmitting infectious diseases such as Hepatitis, AIDS and the like through needles which have become contaminated.

Various prior art arrangements have been proposed but none are as advantageous as the present invention.

SUMMARY OF THE INVENTION

A syringe utilizing the present invention includes a cylindrical hollow barrel member having first and second open ends, and first female thread means on the inside surface of said first end. Also provided is a cylindrically shaped needle holder body having a longitudinal axis, first and second axial ends and further comprising: (i) first male thread means on the curved outer surface thereof and adapted to coact with said first female thread means, and (ii) means on said first axial end for receiving and holding an elongated hollow needle means. The needle holder body additionally has a first recess in said second axial end extending axially along said longitudinal axis to a depth part way toward said first axial end, said first recess having a stoppage protrusion means extending radially inwardly; a second recess in said second axial end extending along said longitudinal axis a depth less than said depth of said first recess, said second recess having a radial extent greater than said first recess; a central penetrating bore extending through said holder body long said longitudinal axis; and first ratational torque transmitting means connected to said body and located in said second recess.

Other components of the syringe are an elongated piston rod; and a piston means having inner and outer axial ends and further comprising: (i) means connecting said inner axial end to one end of said piston rod, (ii) an integral central axially extending protrusion on said outer axial end adapted to fit within said first recess of said needle holder body, and including a stoppage means adapted to coact with said stoppage protrusion means of said first recess so as to lock said piston means to said needle holder body, and (iii) second rotational torque transmitting means on said outer axial end and adapted to coact with said rotational torque transmitting means.

All of the aforementioned items or components are characterized whereby said needle holder body may be initially positioned in said hollow barrel member with said first female thread means engaging said first male thread means, said piston means being insertable into second open end of said barrel member and, upon axial relative movement therebetween, to cause the flow of fluid through said central penetrating bore of said needle holder body and attached hollow needle means, and whereby upon said piston means being inserted, as aforesaid, and axially displaced, relative to said barrel member, to a maximum depth whereat (i) said piston axially extending protrusion is positioned and locked within said first recess of said body with said piston stoppage means engaged with said body stoppage protrusion means, and (ii) said first and second rotational torque transmitting means are engaged, so that, upon rotational torque being applied to said piston rod, said torque is transmitted via said piston means to said body to cause rotation of said body relative to said barrel member and release of said first male thread means from said first female thread means following which axial movement of said locked piston means and said body relative to and into said barrel member is facilitated, said last mentioned axial movement being sufficient to withdraw a needle means on said body, as aforesaid, completely within said first open end of said barrel member, thus preventing accidental contact of said needle means by an errant body part.

The syringe may be further characterized by said means on said first axial end of said needle holder body being a second female thread means; by said first and second rotational torque transmitting means being coacting longitudinally extending protrusions on said body and said piston means; and/or by said barrel member and said piston rod having coacting locking means permitting insertion of said piston into said barrel and locking said piston rod so as to prevent removal of said piston means and attached body.

DESCRIPTION OF THE DRAWINGS

FIG. 2 and FIG.3 show the entire syringe in longitudinal, cross section. FIG. 2 shows the piston within the barrel but spaced longitudinally or axially from the needle holder body while FIG. 3 shows the piston in locked relationship with said body, FIGS. 4 and 5 show details of the syringe on an enlarged basis, FIG. 6 shows the syringe with the needle withdrawn into the barrel, and FIG. 7 shows a modified needle attachment means.

DETAILED DESCRIPTION OF THE PREFERRED EMBODIMENT OF THE INVENTION

Figure 1:
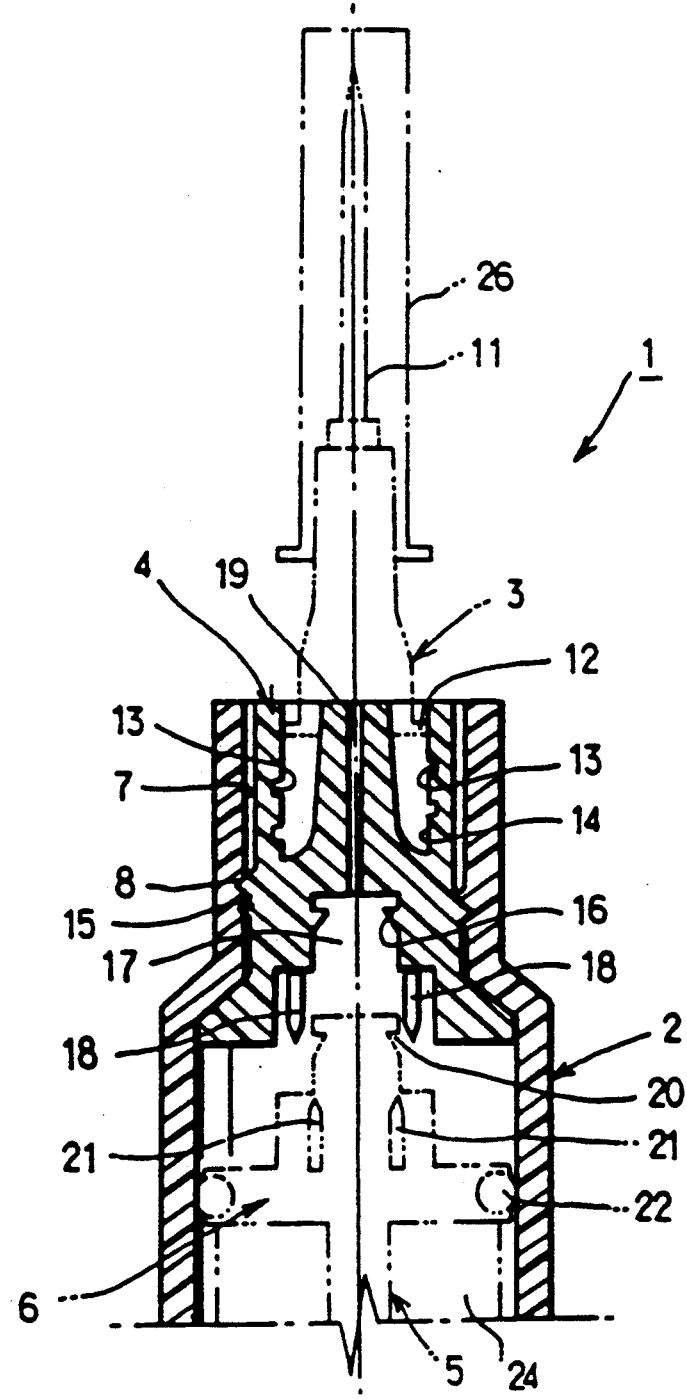
FIG. 1 is a view, in cross section, of the cylindrical hollow barrel with the needle holder body positioned in one end of the barrel.

Referring to the figures, the reference numeral 1 generally depicts the improved syringe and the reference numeral 2 designates the hollow cylindrical barrel member having first and second open ends. First female thread means 8 are provided on the inside curved surface 7 of the first end of the hollow barrel. A cylindrically shaped needle holder body 4 has a longitudinal axis and first and second axial ends and further comprises first male thread means 15 on the curved outer surface thereof which are adapted to coact with said first female thread means 8. The body also has means on said first axial end thereof for receiving and holding an elongated hollow needle means, more specifically, an annular recess extending axially from the first axial end with second female thread means 13 disposed in the outer surface 14 of said annular recess. A standard holder 3 for a standard needle 11 and having a radially extending shoulder 12 at one end thereof is adapted to be threaded into the annular recess through the coaction of the shoulder 12 and the female threads 13.

The second axial end of the body has a first recess 17 extending longitudinally to a depth partway toward said first axial end of the body. The body has a stoppage protrusion means in the form of an annular shoulder 16 extending radially inwardly in recess 17 toward the longitudinal axis as most clearly shown in FIG. 1. The shoulder 16 extends around the body's longitudinal axis and is sloped from its inner tip toward the second open end of the barrel; the other surface of the protrusion is radially away from the longitudinal axis thus forming a shoulder which is normal to the longitudinal axis.

The body has a second recess in said second axial end extending along the longitudinal axis a depth less than the depth of recess 17 but having a greater radial extent measured from the longitudinal axis than recess 17.

The body also has a central bore 19 extending therethrough along the longitudinal axis. the body further has first rotational torque transmitting means 18 shown as longitudinal extending rib portions shown clearly in FIGS. 1, 2 and 4–7. The ribs extend radially toward the longitudinal axis a preselected distance and longitudinally a preselected distance.

An elongated piston rod 5 is provided consisting of a plurality of laterally extending flutes 24 emanating from the longitudinal axis and having at one end thereof an end piece 23 integral therewith so as to provide a means for moving the piston rod 5 in and out of the hollow barrel 2 along the longitudinal axis and further to permit the application of rotational torque to the piston rod by manual rotation of the piston (relative to the barrel about the longitudinal axis.

A piston means 6 is affixed to the other end of the piston rod 5; it has a generally circular cross-section and a relatively short axial or longitudinal extent thus defining an inner axial end which is adapted to be attached to or integral with the piston rod 5 and an outer axial end or face from which depends a centrally located axially extending protrusion, shown in all figures but expecially well (in phantom form) in FIG. 1, wherein it is seen that the said protrusion is shaped in a complementary form with respect to the recess 17 and its associated larger diameter recess including a circumferential groove 20 adapted to coact with annular shoulder 16. The piston 6 further has a circumferencial flexible gasket 22 of a diameter selected so that when the piston 6 with the gasket 22 mounted thereon is positioned within the barrel 2, as shown in the figures, there will be a tight sliding fit between the piston assembly and the barrel to permit, when desired, the forcing or pumping of liquid within the barrel 2 out through the passageway 19 and the connected needle 11 or, in the other mode of operation, to pull fluid from an external source through the needle 11, passageway 19, and into the barrel 2.

The piston assembly further includes second rotational torque transmitting means 21 on said outer axial end of the piston 6 which are adapted to coact with said first rotational torque transmitting means 18. The specific means shown are a plurality of longitudinally extending and also radially inwardly extruding ribs arranged around the periphery of the piston assembly protrusion. The ribs 21 are dimensioned to coact with the ribs 18 upon a preselected rotational relationship between the piston assembly 6 and the body 4; when this relationship is established, then the piston assembly may be moved axially toward the body so as to be in complete engagement with the body as is depicted in FIGS. 2-7. Once such total engagement is reached, the inwardly extending annular shoulder 16 will be "snapped" into position in the notch 20 of the piston assembly.

The piston assembly further includes a notch 25 in one or more of the fins or flutes 24 of the piston assembly; two such notches 25 are shown in FIGS. 2-7. The notches 25 are adapted to coact with radially inwardly extending shoulders or latch means 9 with the cooperating surfaces being beveled to permit the piston assembly to move inwardly into the barrel 2 but the shoulder 9 serves as a latch by catching notches 25 to prevent the piston assembly from being withdrawn any further than the latch position as is depicted in FIG. 6 where the piston assembly, latched to the body 4 with the associated needle holder 3 and needle 11 has been withdrawn within the barrel a sufficient longitudinal extent so that the sharp pointed tip on the needle 11 is within the open end of the barrel.

Thus in practice the barrel 2 and body 4 would be preassembled at the factory; the piston assembly would also be, in the usual case, already positioned within the barrel 2 as shown in FIG. 2.

When medical personnel intend to use the syringe, then the needle holder 3 and needle 11 would be connected to the body 4 as is shown in FIGS. 2-7. At this point the syringe can be used, as is well understood, either to inject fluid from within the syringe into a patient or to withdraw a fluid sample, e.g., blood, from a patient and collect it in the barrel.

Upon completion of the use of the syringe as intended, then in order to render the syringe safe from an accidental stick, the piston assembly is then forced longitudinally up into engagement with the body 4 by having the protrusion on the piston assembly placed into full engagement with the corresponding recess 17 of the body 4, all as aforesaid. In this position the firs and second rotational torque transmitting means 18 and 21 are in operative engagement so that, when rotational torque is applied to the handle piece 23 of the piston assembly of the correct sense, and the barrel 2 is held, then the body 4 is unthreaded and released from the barrel 2, the body 4 being carried along with the piston assembly due to the locking action of elements 16 with 20. Once the threads 8 and 15 have become disengaged, then the piston assembly may be further moved in a longitudinal direction away from the first end of the barrel to a point where it is latched through the coaction between the shoulder 9 and the notches 25; at this point the dangerous sharp tip to the needle 11 is out of harms way by being completely within the first open end of the barrel member, an accidental contact of said point on the needle means by an errant body part being thus prevented.

In FIG. 1 the reference numeral 26 depicts a standard protective outer cap which may be used to safeguard the needle until actual use of the syringe is intended.

FIG. 7 shows an alternative embodiment wherein the needle holder 3 fits tightly on a central extension 27 of the body instead of coacting with the threads 13 on the inside surface 14 of the body 4, as described above.

Referring again to the embodiment shown in FIGS. 1-6, the preferred amount of threaded engagement between the male threads 15 on the body 4 and the female threaded portion 8 of the hollow barrel 2 is approximately one-fourth to one turn. It may be assumed, by way of example, that it takes a relative clockwise rotation of the body 4 with respect to the barrel 2 to have the threaded engagement of the body with the barrel as is depicted, for example, in FIGS. 1-6. After completion of the usage of the syringe, as described above, then the rotational torque applied to element 23 of the piston assembly will apply a relative counter clockwise rotation or torque to the body 4, with respect to the barrel 2, thus disengaging the body, as aforesaid, from the barrel 2 to permit the subsequent withdrawal of the needle assembly within the barrel as is clearly depicted in FIG. 6.

I claim:

1. A safety syringe comprising:
   (a) a cylindrical hollow barrel member adapted to contain a fluid and having first and second open ends and a female thread on the inside surface of said first end, said female thread being preselected to mate with a male thread on a needle holder body;
   (b) a cylindrically shaped needle holder body having a longitudinal axis, first and second axial ends and further comprising:
       (i) a male thread on the curved outer surface thereof and being preselected to mate with said female thread,
       (ii) means on said first axial end for receiving and holding the hub of an elongated hollow needle,
       (iii) a recess in said second axial end extending axially along said longitudinal axis to a depth part way toward said first axial end,
       (iv) first means for transmitting rotational torque integral with said body and located in said recess, and
       (v) a central bore extending through said holder body along said longitudinal axis;
   (c) an elongated hollow needle including a hub, said hub exclusively held by said hub receiving and holding means;
   (d) an elongated piston rod; and
   (e) a piston having inner and outer axial ends and further comprising:
       (i) means connecting said inner axial end thereof to one end of said piston rod,
       (ii) an integral central axially extending protrusion on said outer axial end thereof constructed to fit within said recess of said needle holder body, and including;
           (1) second means for transmitting rotational torque integral with said protrusion and constructed to coact with said first rotational torque transmitting means,
           (2) snap locking means on said protrusion and said holder body for snap locking said protrusion to said holder body;

whereby said needle holder body may be initially positioned in said hollow barrel member with said female thread engaging said male thread, and said piston on said piston rod may be inserted into said second open end of said barrel member so that, upon relative axial displacement therebetween, fluid within said barrel is pumped through said central bore of said needle holder body and said hollow needle exclusively held thereon, and whereby, upon said piston being inserted, as aforesaid, and axially displaced, relative to said barrel member, to a position whereat said piston central axially extending protrusion is positioned within said recess of said body with said second rotational torque transmitting means thereon engaged with said first rotational torque transmitting means of said body and with said snap locking means locking said protrusion with said body, then upon rotational torque being applied to said piston rod, said torque is transmitted via said protrusion to said body to cause rotation of said body relative to said barrel member to thereby release said male thread from said female thread following which axial movement of said locked protrusion and said body relative to said barrel member is facilitated, said last mentioned axial movement being sufficient to withdraw said needle completely within said first open end of said barrel member, thus preventing accidental contact of said needle means by an errant body part.

2. Apparatus of claim 1 further characterized by said first and second rotational torque transmitting means being a plurality of longitudinally extending ribs, the ribs on said body extending radially inward and the ribs on said piston central protrusion extending radially outward.

* * * * *